United States Patent
Sato et al.

(10) Patent No.: US 6,372,830 B1
(45) Date of Patent: Apr. 16, 2002

(54) WATER-IN-OIL TYPE SILICONE EMULSION COMPOSITIONS

(75) Inventors: Yoshiyuki Sato, Ohta (JP); John A. Kilgour, Clifton Park, NY (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/394,669

(22) Filed: Sep. 13, 1999

(30) Foreign Application Priority Data

Sep. 14, 1998 (JP) .................................. 10-260196

(51) Int. Cl.[7] .............................. C08J 3/02; C08K 5/06; C08L 83/10; A61K 7/00; B01F 17/52
(52) U.S. Cl. ................. 524/266; 524/261; 524/588; 516/23; 424/65; 424/401; 514/938
(58) Field of Search .................. 516/23; 524/588, 524/266, 261; 424/65, 401; 514/937, 938; 525/474, 477

(56) References Cited

U.S. PATENT DOCUMENTS

| | | | | |
|---|---|---|---|---|
| 4,532,132 A | * | 7/1985 | Keil | 514/937 |
| 5,015,469 A | * | 5/1991 | Yoneyama et al. | 514/938 |
| 5,470,563 A | * | 11/1995 | Tanaka et al. | 424/63 |
| 5,955,003 A | * | 9/1999 | Terren et al. | 516/23 |
| 6,210,690 B1 | * | 4/2001 | Nabeshima et al. | 424/401 |

FOREIGN PATENT DOCUMENTS

| | | | |
|---|---|---|---|
| JP | 8-268831 | * | 10/1996 |
| JP | 8-268832 | * | 10/1996 |
| WO | WO 98/38970 | * | 9/1998 |

OTHER PUBLICATIONS

Database WPI on Dialog, week 199651, London: Derwent Publications Ltd., AN 96–514856, Class A26, JP 8268831 A (Shiseido Co Ltd), abstract, 1996.*

Database WPI on Dialog, week 199651, London: Derwent Publications Ltd., AN 96–514857, Class A26 (Shiseido Co Ltd) abstract, 1996.*

* cited by examiner

Primary Examiner—Daniel S. Metzmaier

(57) ABSTRACT

Disclosed is a water-in-oil type silicone emulsion composition, which has excellent stability to temperature changes, particularly to those including low-temperature regions and which undergoes no separation of the oil or water phase, the composition comprising (A) a polyorganosiloxane; (B) a polyorganosiloxane-polyoxyalkylene block copolymer of a specific structure having polyoxyalkylene chains at each terminal end of the polyorganosiloxane chain and as side chains thereof, the polyorganosiloxane chain having a polymerization degree of 300 to 600; and (C) water.

2 Claims, No Drawings

WATER-IN-OIL TYPE SILICONE EMULSION COMPOSITIONS

BACKGROUND OF THE INVENTION

The present invention relates to a water-in-oil type silicone emulsion composition, more particularly to a water-in-oil type silicone emulsion composition having excellent stability to temperature changes, high safety against the skin and excellent texture when applied to the skin.

DESCRIPTION OF THE RELATED ART

Silicone fluids and gumlike siloxane high polymers, so-called silicone gums, are characterized in that they are physiologically highly safe, hardly deteriorate and have excellent water repellency, and cosmetics containing such high polymers, when applied to the skin or the like, spread well, are less tacky and impart oil-free and smooth touch and gloss to the skin, so that they are widely employed cosmetic ingredients. Meanwhile, cyclic dimethylsiloxane oligomers are employed as ingredients for antiperspirants and the like because of their excellent compatibility with silicone fluids and hydrocarbon cosmetic ingredients, excellent spreadability and absence of chilliness when they volatilize.

There are disclosed a number of techniques for obtaining stable oil-in-water type emulsions of polyorganosiloxanes by means of emulsion polymerization using ordinary surfactants as emulsifiers or in the presence of specific emulsifiers. However, water-in-oil type emulsion compositions of polyorganosiloxanes are not yet successful in exhibiting satisfactory stability to temperature changes.

As a method for obtaining water-in-oil type emulsion compositions of polyorganosiloxanes, there is known a technique of employing various kinds of lipophilic polyorganosiloxane-polyoxyalkylene block copolymers as emulsifiers. It should be noted here that the block copolymers referred to herein mean those each having a linear polyorganosiloxane as the main chain and polyoxyalkylene chains at the terminal ends and/or as side chains and include so-called graft copolymers having polyoxyalkylene chains as side chains only.

For example, Japanese Provisional Patent Publication Nos. 66752/1986, 212321/1986, 212324/1986, 218509/1986, 45656/1987 and 54759/1987 disclose water-in-oil type emulsion compositions of polyorganosiloxanes prepared by using block copolymers of various structures as emulsifiers and by adding organically modified clay minerals. In Examples of these official gazettes, there are employed as such polyorganosiloxanes containing polyoxyalkylene chains at each terminal end and as side chains those having relativity low viscosity values of 60 to 200 cSt at 25° C. While it is reported that these compositions are stable at temperatures of 0 to 50° C. and are also stable to a temperature cycle between 5 and 45° C., they failed to show sufficient stability to temperature cycles including cooling to a low temperature of −10° C.

Japanese Provisional Patent Publication No. 215510/1987 discloses water-in-oil type emulsion compositions of polyorganosiloxanes prepared by using like polyorganosiloxane-polyoxyalkylene block copolymers as emulsifiers and containing in the aqueous phases organic salts respectively. Meanwhile, it is disclosed in Japanese Provisional Patent Publication Nos. 216635/1987, 119844/1988, 180237/1989 and 88513/1989 to prepare like water-in-oil type emulsion compositions using like polyorganosiloxane-polyoxyalkylene block copolymers in combination with other surfactants, gelling agents, etc. Of the block copolymers employed in Examples of these official gazettes, those having polyoxyalkylene chains at each terminal end and as side chains all have polyorganosiloxane chains with polymerization degrees in the range of 64 to 162. However, none of these emulsion compositions have sufficient stability to temperature cycles.

Meanwhile, it is disclosed in Japanese Provisional Patent Publication Nos. 203466/1989 and 93136/1993 to effect emulsification of polyorganosiloxanes using as emulsifiers block copolymers each having a polyoxyalkylene chain at one terminal end of the polyorganosiloxane chain having 50 or less or 150 or less silicon atoms to provide water-in-oil type emulsion compositions having excellent stability to dilution. However, those emulsions obtained using such emulsifiers still do not have sufficient stability to temperature cycles.

Further, it is disclosed in Japanese Provisional Patent Publication Nos. 24959/1979, 268831/1996, and 268832/1996 to use polyorganosiloxane-polyoxyalkylene block copolymers including those of high-molecular weight region as emulsifiers to prepare water-in-oil type emulsion compositions of polyorganosiloxanes. Of the block copolymers employed in examples of these official gazettes, those of the type having polyoxyalkylene chains at each terminal end and as side chains have high polyorganosiloxane chain polymerization degrees of 1.011, and none of emulsion compositions of these block copolymers are successful in satisfying both stability as emulsions per se and stability to temperature cycles.

As a result of out studies, such block copolymers having polyorganosiloxane chains of low polymerization degrees generally provide emulsion compositions having poor stability to temperature cycles, whereas those having polyorganosiloxane chains of high polymerization degrees exhibit poor effects as emulsifiers, and the resulting emulsion compositions per se come to have poor stability.

SUMMARY OF THE INVENTION

An objective of the present invention is to provide water-in-oil type emulsion compositions of polyorganosiloxanes which are stable as emulsions per se and show excellent stability to temperature changes particularly to those including cooling to low-temperature regions of −5° C. or lower and which cause no oil phase and/or aqueous phase separation. Another objective of the present invention is to provide a water-in-oil type emulsion composition which has excellent stability to the temperature changes as described above and is incorporated with components necessary for cosmetics and the like such as salts.

We made studies with a view to attaining the above objectives to find that the intended objectives can be attained by using as an emulsifier a block copolymer having a molecular structure within a specific range where polyoxyalkylene chains are present at each terminal end and as side chains of a polyorganosiloxane chain having a polymerization degree within a specific range and accomplished the present invention.

To describe more specifically, the water-in-oil type emulsion composition according to the present invention is characterized in that it contains:

(A) at least one sort of polyorganosiloxane;
(B) at least one sort of polyorganosiloxane-polyoxyalkylene block copolymer represented by the general formula (I):

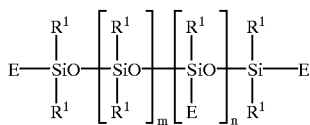

(I)

wherein R$^1$s each represent a methyl group and some of R$^1$s may be phenyl groups; Es each represent a group of the general formula (II):

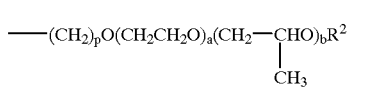

(II)

wherein R$^2$ represents a hydrogen atom, an acyl group or an alkyl group having 1 to 4 carbon atoms; p is an integer of 3 to 6; a is an integer of 2 to 50; b is an integer of 0 to 50; and a+b is an integer of 5 to 100; m is an integer of 300 to 600; n is an integer of 1 to 30; and m+n is an integer of 300 to 600; and (C) water.

MODE FOR CARRYING OUT THE INVENTION

The component (A) employed in the emulsion composition of the present invention is a polyorgano-siloxane constituting the oil phase as a continuous phase and includes silicone fluids ranging from those of low-viscosity values to high-viscosity values and gumlike siloxane high polymers which may be linear or contain small amounts of branched siloxane structures. The component (A) also includes linear or cyclic siloxane oligomers, trimethylsiloxysilicic acid and cyclic compounds thereof. The organic groups bonded to the silicon atoms include linear or branched alkyl groups such as methyl, ethyl, propyl, butyl, pentyl, hexyl, octyl, decyl, dodecyl, tetradecyl, hexadecyl and octadecyl; cycloalkyl groups such as cyclohexyl; aralkyl groups such as 2-phenylethyl and 2-phenylpropyl; alkenyl groups such as vinyl and allyl; aryl groups such as phenyl and tolyl; and substituted monovalent hydrocarbon groups such as 3,3,3-trifluoropropyl, 3-aminopropyl and 3-(2-aminoethyl)-aminopropyl, and the organic groups may be of one or more sorts.

The silicone fluids and gumlike siloxane high polymers can be exemplified by polydimethylsiloxane, polymethylphenylsiloxane, polymethylvinylsiloxane, polymethyl(higher alkyl)-siloxane, polymethyl(3,3,3-trifluoropropyl)siloxane, polymethyl(3-aminopropyl)-siloxane and polymethyl[3-(2-aminoethyl)aminopropyl]-siloxane; whereas the siloxane oligomers can be exemplified by octamethylcyclotetrasiloxane and decamethylcyclopentasiloxane. These silicone fluids and gumlike siloxane high polymers may be used alone or as a combination of two or more sorts, for example, a mixed siloxane prepared by dissolving a gumlike siloxane high polymer in a cyclic siloxane. Further, they may be used in the form of solution in hydrocarbon solvents such as n-hexane and xylene.

When the resulting emulsion compositions are used as cosmetics, silicone fluids such as polydimethylsiloxane, polymethylphenylsiloxane, polymethyl(3-aminopropyl)-siloxane and polymethyl[3-(2-aminoethyl)aminopropyl]-siloxane; gumlike siloxane high polymers such as polydimethylsiloxane; and cyclic siloxane oligomers such as octamethylcyclotetrasiloxane and decamethylcyclopentacyloxane are preferred among others.

While the content of the component (A) in the silicone emulsion composition may not particularly be limited, it is usually 5 to 90% by weight, preferably 10 to 80% by weight, and more preferably 15 to 60% by weight.

The polyorganosiloxane-polyoxyalkylene block copolymer of the component (B) employed in the emulsion composition of the present invention is an emulsifier for effecting emulsification of the oil-phase polyorgano-siloxane, the aqueous-phase water and other components added as necessary to form a water-in-oil type emulsion composition. What is characteristic to the present invention is that a water-in-oil type silicone emulsion composition which is stable to temperature cycles including cooling to low temperature regions of −5° C. or lower can be obtained by using a polyorganosiloxane-polyoxyalkylene block copolymer within a specific range to be described below as the emulsifier.

The component (B) described above is represented by the general formula (I):

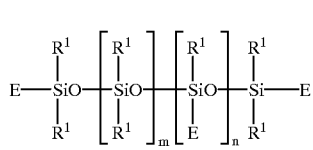

(I)

wherein R$^1$, E, m and n have the same meanings as defined above, respectively.

It should be noted here that in the general formula (I), m and n merely represent the numbers of the two sorts of inner siloxane units, respectively, and these two sorts of inner units are arranged at random. R$^1$s each represent a methyl group, and some of R$^1$s (e.g., up to 40 mol %) may be phenyl groups.

m representing the number of the inner diorgano-siloxane units containing no E is an integer of 300 to 600. n representing the number of the inner siloxane units in which E is bonded to the silicon atom is an integer of 1 to 30, preferably 3 to 15. However, the polymerization degree of the units m+n, i.e. the polysiloxane chain excluding the both terminal end units, is 300 to 600. If the polymerization degree of the units m+n is less than 300, the resulting emulsion composition shows poor stability to temperature cycles including low-temperature regions; whereas if it exceeds 600, the resulting emulsion per se comes to have poor stability.

E is a group containing a polyoxyalkylene chain. What is characteristic to the component (B) employed in the present invention is that E is present at each terminal end of the polysiloxane and as side chains in some of the inner units thereof. E is represented by the general formula (II):

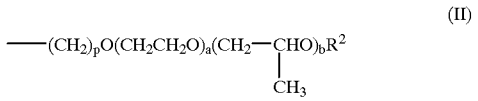

(II)

wherein R$^2$, p, a and b have the same meanings as defined above, respectively.

In the general formula (II), a and b merely represent the number of oxyethylene units and that of the oxypropylene units in E, respectively. While these two sorts of units are usually arranged at random in the E chain, they may be arranged blockwise, for example, in the form of blockcopolymized chain such that the oxyalkylene moiety consisting of the oxypropylene units may be located on the siloxane side.

p is an integer of 3 to 6 so as to obtain excellent chemical stability between the silicon atoms and the polyoxyalkylene chains, particularly preferably 3 so as to facilitate synthesis and handling. a is an integer of 2 to 50, preferably 5 to 30; and b is an integer of 0 to 50, preferably 0 to 20. That is, the polyoxyalkylene moiety of E is either a polyoxyethylene chain or an oxyethylene-oxypropylene copolymer chain, with the proviso that a+b is an integer of 5 to 100, preferably 10 to 80. If a and b are not within the specified ranges, the composition of the present invention comes to have poor stability.

$R^2$ is the terminal group of E and is exemplified by a hydrogen atom; an acyl group such as acetyl; and an alkyl group such as methyl, ethyl, propyl and butyl.

While the component (B) may be in the form of liquid, semi-solid or solid at ambient temperature, it is preferably liquid at 25° C. in view of ease of handling.

The component (B) can be exemplified by those represented by the following formulae (III) to (VI):

It should be noted that in the above and the following formulae, two sorts of inner siloxane units in the polyorganosiloxane chain and two sorts of oxyalkylene units in the polyoxyalkylene chain are arranged at random, respectively.

The component (B) can be synthesized as follows. For example, there is synthesized a polyorganohydrogensiloxane having a hydrogen atom bonded to a silicon atom in each terminal group to which E is to be incorporated and in some of the inner units. A polyoxyalkylene having at one terminal end $R^2$ and at the other end an alkenyl group such as an allyl group is added to the polyorganohydrogen-siloxane and the resulting mixture is heated in the presence of a platinum catalyst to bring about an addition reaction between the Si—H bond in the polyorganohydrogen-siloxane and the alkenyl group of the polyoxyalkylene, and thus the polyoxyalkylene is introduced into the poly-organosiloxane to synthesize a block copolymer as the component (B). The platinum catalyst can be exemplified chloroplatinic acid, a platinum complex obtained by heating chloroplatinic acid and an alcohol, a platinum-olefin complex and a platinum-vinylsiloxane complex.

While the content of the component (B) in the silicone emulsion composition may not particularly be limited, it is preferably 0.1 to 30% by weight, more preferably 0.5 to 10% by weight.

(III)

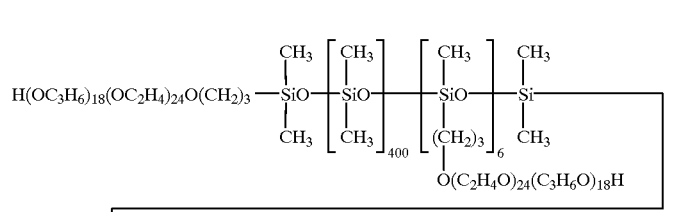

(IV)

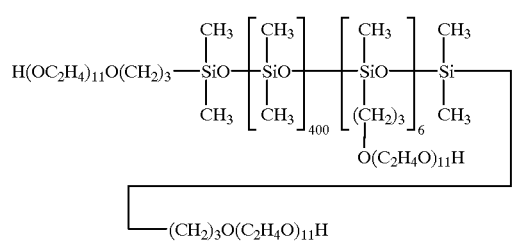

(V)

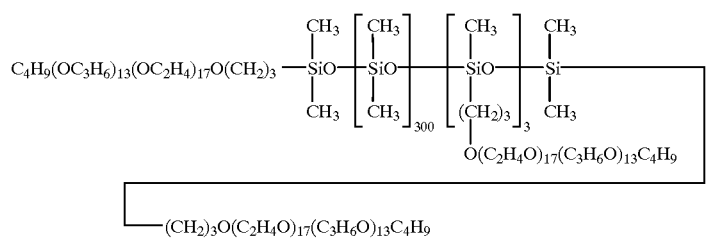

(VI)

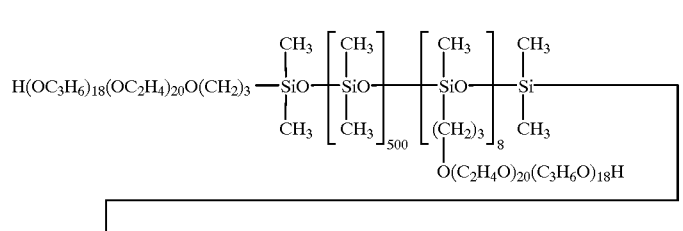

In the present invention, the component (C) is water and constitutes the aqueous phase as a dispersed phase in the emulsion composition of the present invention. While the content of the component (C) in the silicone emulsion composition may not particularly be limited, it is preferably 5 to 80% by weight, more preferably 10 to 50% by weight.

The salt to be added optionally to the emulsion composition of the present invention may not particularly be limited so long as it does not impair stability of the emulsion to temperature changes, which is the feature of the present invention, and is exemplified by aluminum salts such as aluminum chloride, aluminum chlorohydrate and aluminum citrate; aluminum-zirconium double salts such as aluminum-zirconium tetrachlorohydrate and aluminum-zirconium tetrachlorohydrate-glycine complex; zinc salts such as zinc chloride, zinc sulfate, zinc undecylenoate, zinc palmitate, zinc stearate and zinc p-phenolsulfonate; and salts of amino acids such as glycine, alanine, valine, leucine, isoleucine, serine, aspartic acid and glutamic acid.

The content of the salts to be added to the emulsion composition is usually up to 50% by weight, and those salts which are known as astringent agents including, for example, aluminum salts, aluminum-zirconium double salts and zinc salts are preferably added in an amount of 5 to 30% by weight in view of their effects, stability, particularly excellent stability to temperature changes, of the resulting emulsion.

The emulsion compositions of the present invention can be incorporated with polyhydric alcohols such as propylene glycol, 1,3-butylene glycol, glycerol, sorbitol and polyethylene glycol, and addition of such polyhydric alcohols is preferred since they can improve moisturizing effects of the resulting emulsion compositions when they are employed as cosmetics.

Further, the emulsion composition of the present invention may be incorporated with a surfactant other than the component (B), an antioxidant, an antiseptic, a antifungi agent, a humectant, a UV absorber, a lower alcohol, a perfume, an extender pigment, a color pigment, etc., so long as the effect of the present invention is not impaired.

The emulsion composition of the present invention can be prepared by premixing the components (A), (B) and (c), and other components which are added optionally and then emulsifying the resulting mixture using conventional emulsifying means such as a homomixer and a homogenizer.

DETAILED DESCRIPTION OF THE PREFERRED EMBODIMENTS

The present invention will be described below more specifically by way of Examples and Comparative Examples, in which part(s) means part(s) by weight, and the viscosity values were measured at 25° C. The present invention is not to be limited to these Examples.

Examples 1 to 4 and Comparative Examples 1 to 3

Water-in-oil type emulsions were prepared using the ingredients according to the formulations shown in Table 1, respectively. The block copolymers of the formulae (III) to (VI) exemplified above as the component (B) were employed as the polyorganosiloxane-polyoxyalkylene block copolymers in Examples 1 to 4, respectively; while block copolymers of the following formulae (VII) to (IX):

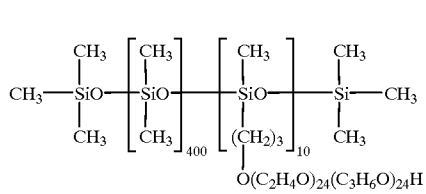

(VII)

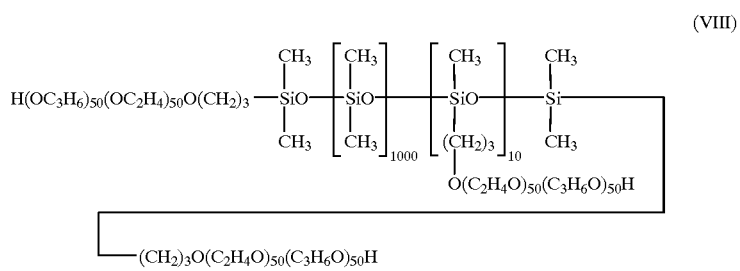

(VIII)

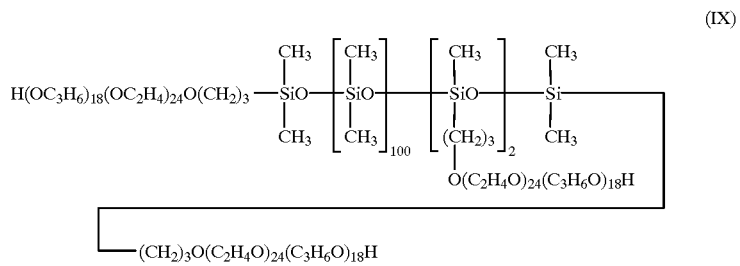

(IX)

were employed in Comparative Examples 1 to 3, respectively.

That is, the components (1), (2) and (3) were charged into a mixing tank, and the resulting mixture was mixed with stirring under heating to 70° C., to which the component (5) was admixed to prepare an oily matter. Meanwhile, the components (4) and (6) were dissolved in the component (7) to prepare an aqueous solution. The aqueous solution was dropped to the oily matter under stirring with a homomixer, followed by further stirring well of the mixture in the homomixer after completion of dropping to prepare a water-in-oil type silicone emulsion composition to be employed as a hand moisture lotion.

Examples 5 to 8 and Comparative Examples 4 to 6

Water-in-oil type emulsions were prepared using the raw materials according to the formulations shown in Table 2, respectively.

TABLE 1

| | Component | Formulation (Part) Example 1 | 2 | 3 | 4 | Comp. Example 1 | 2 | 3 |
|---|---|---|---|---|---|---|---|---|
| (1) | Polydimethylsiloxane (10 cSt) | 43.5 | 43.5 | 43.5 | 43.5 | 43.5 | 43.5 | 43.5 |
| (2) | Polyorganosiloxane-polyoxyalkylene block copolymer | | | | | | | |
| | (III) | 5.0 | — | — | — | | | |
| | (IV) | — | 5.0 | — | — | | | |
| | (V) | — | — | 5.0 | — | | | |
| | (VI) | — | — | — | 5.0 | | | |
| | (VII) | — | — | — | — | 5.0 | — | — |
| | (VIII) | — | — | — | — | — | 5.0 | — |
| | (IX) | — | — | — | — | — | — | 5.0 |
| (3) | Sorbitan monolaurate | 1.5 | 1.5 | 1.5 | 1.5 | 1.5 | 1.5 | 1.5 |
| (4) | Methyl p-hydroxy-benzoate | 0.1 | 0.1 | 0.1 | 0.1 | 0.1 | 0.1 | 0.1 |
| (5) | Propyl p-hydroxy-benzoate | 0.1 | 0.1 | 0.1 | 0.1 | 0.1 | 0.1 | 0.1 |
| (6) | 1,3-Butylene glycol | 10.0 | 10.0 | 10.0 | 10.0 | 10.0 | 10.0 | 10.0 |
| (7) | Water | 39.8 | 39.8 | 39.8 | 39.8 | 39.8 | 39.8 | 39.8 |

TABLE 2

| | Component | Formulation (Part) Example 5 | 6 | 7 | 8 | Comp. Example 4 | 5 | 6 |
|---|---|---|---|---|---|---|---|---|
| (1) | Octamethylcyclotetrasiloxane | 19.0 | 19.0 | 19.0 | 19.0 | 19.0 | 19.0 | 19.0 |
| (2) | Polyorganosiloxane-polyoxyalkylene block copolymer | | | | | | | |
| | (III) | 1.0 | — | — | — | | | |
| | (IV) | — | 1.0 | — | — | | | |
| | (V) | — | — | 1.0 | — | | | |
| | (VI) | — | — | — | 1.0 | | | |
| | (VII) | — | — | — | — | 1.0 | — | — |
| | (VIII) | — | — | — | — | — | 1.0 | — |
| | (IX) | — | — | — | — | — | — | 1.0 |
| (3) | Aluminum zirconium tetrachlorohydrate/glycin complex (50% aqueous solution) | 40.0 | 40.0 | 40. | 40.0 | 40.0 | 40.0 | 40.0 |
| (4) | Propylene glycol | 26.0 | 26.0 | 26.0 | 26.0 | 26.0 | 26.0 | 26.0 |
| (5) | Ethanol | 7.0 | 7.0 | 7.0 | 7.0 | 7.0 | 7.0 | 7.0 |
| (6) | Water | 7.0 | 7.0 | 7.0 | 7.0 | 7.0 | 7.0 | 7.0 |

That is, the components (1) and (2) were charged into a mixing tank, and the resulting mixture was heated at 70° C. with stirring to prepare an oily matter. Meanwhile, the component (3) was dissolved in a mixture of the components (4) to (6) to prepare an aqueous solution. The aqueous solution was dropped to the oily matter under stirring with a homomixer, followed by further stirring well of the mixture in the homomixer after completion of dropping to prepare a water-in-oil type silicone emulsion composition to be employed as an antiperspirant.

Evaluation Example 1

The emulsion compositions prepared in Examples and Comparative Examples respectively were subjected to a temperature cycle test (between −10° C. and 25° C.×24 hours/cycle) as shown below to follow up viscosity changes up to 10 cycles. It should be noted here that evaluation was discontinued for those samples in which separation of the water phase and the aqueous phase was observed.

| Temperature cycle conditions: | −10° C. × 16 hrs. |
|---|---|
| | 25° C. × 8 hrs. |

Viscosity of each emulsion composition before subjected to the temperature cycle test was measured as the initial viscosity. Viscosity of each sample was measured cyclewise in 10 cycles after it was maintained at 25° C. for 7 hours, and the rate of viscosity change in the cycle where the sample showed the maximum viscosity change in terms of absolute value was determined according to the following equation:

$$\text{Rate of viscosity change (\%)} = \frac{\text{Maximum viscosity difference}}{\text{Initial viscosity}} \times 100$$

Evaluation results of the water-in-oil type emulsion compositions prepared in Examples 1 to 4 and Comparative Examples 1 to 3 are shown in Table 3, and those obtained for the water-in-oil type emulsion compositions prepared in Examples 5 to 8 and Comparative Examples 4 to 6 are shown in Table 4.

TABLE 3

| | | Example | | | | Comparative Example | | |
|---|---|---|---|---|---|---|---|---|
| | Cycle | 1 | 2 | 3 | 4 | 1 | 2 | 3 |
| Viscosity (cSt) | Initial | 74,000 | 52,000 | 48,000 | 66,000 | 68,000 | 86,000 | 14,000 |
| | 1 | 74,000 | 52,000 | 48,000 | 66,000 | 68,000 | 86,000 | 14,000 |
| | 2 | 74,000 | 52,000 | 48,000 | 66,000 | 60,000 | 80,000 | 10,000 |
| | 3 | 74,000 | 52,000 | 46,000 | 64,000 | 60,000 | 72,000 | Separated |
| | 4 | 74,000 | 50,000 | 46,000 | 64,000 | 56,000 | 66,000 | |
| | 5 | 70,000 | 54,000 | 44,000 | 62,000 | 54,000 | 60,000 | |
| | 6 | 70,000 | 50,000 | 46,000 | 62,000 | 50,000 | Separated | |
| | 7 | 72,000 | 50,000 | 44,000 | 60,000 | 46,000 | | |
| | 8 | 72,000 | 52,000 | 44,000 | 64,000 | 44,000 | | |
| | 9 | 74,000 | 54,000 | 46,000 | 64,000 | 42,000 | | |
| | 10 | 72,000 | 50,000 | 44,000 | 62,000 | 38,000 | | |
| Rate of viscosity change (%) | | 5.4 | 3.8 | 8.3 | 9.1 | 44.1 | — | — |

TABLE 4

| | | Example | | | | Comparative Example | | |
|---|---|---|---|---|---|---|---|---|
| | Cycle | 5 | 6 | 7 | 8 | 4 | 5 | 6 |
| Viscosity (cSt) | Initial | 84,000 | 68,000 | 70,000 | 92,000 | 82,000 | 100,000 | 8,600 |
| | 1 | 88,000 | 68,000 | 72,000 | 92,000 | 81,000 | 102,000 | Separated |
| | 2 | 88,000 | 72,000 | 74,000 | 86,000 | 81,000 | 98,000 | |
| | 3 | 84,000 | 68,000 | 76,000 | 86,000 | 78,000 | 90,000 | |
| | 4 | 84,000 | 64,000 | 78,000 | 84,000 | 70,000 | 88,000 | |
| | 5 | 84,000 | 62,000 | 74,000 | 86,000 | 68,000 | 70,000 | |
| | 6 | 84,000 | 64,000 | 70,000 | 86,000 | 68,000 | 62,000 | |
| | 7 | 82,000 | 62,000 | 66,000 | 86,000 | 64,000 | Separated | |
| | 8 | 80,000 | 64,000 | 64,000 | 84,000 | 60,000 | | |
| | 9 | 80,000 | 62,000 | 64,000 | 84,000 | 62,000 | | |
| | 10 | 80,000 | 62,000 | 62,000 | 86,000 | 62,000 | | |
| Rate of viscosity change (%) | | 4.8 | 8.8 | 11.4 | 8.7 | 24.4 | — | — |

Evaluation Example 2

The water-in-oil type emulsion compositions prepared in Examples 1 to 4 and Comparative Examples 1 to 3 respectively were subjected to a temperature cycle test (up to 10 cycles) like in Evaluation Example 1 (between −10° C. and 50° C.×24 hours/cycle) as shown below to follow up viscosity changes, and rates of viscosity change were determined likewise. The viscosity of each sample was measured cyclewise after it was maintained at 50° C. for 7 hours and then left to stand at 25° C. for one hour. The results are shown in Table 5.

| Temperature cycle conditions: | −10° C. × 16 hrs. |
|---|---|
| | 50° C. × 7 hrs. |
| | 25° C. × 1 hr. |

TABLE 5

| | | Example | | | | Comparative Example | | |
|---|---|---|---|---|---|---|---|---|
| | Cycle | 1 | 2 | 3 | 4 | 1 | 2 | 3 |
| Viscosity (cSt) | Initial | 74,000 | 52,000 | 48,000 | 66,000 | 68,000 | 86,000 | 14,000 |
| | 1 | 74,000 | 52,000 | 48,000 | 66,000 | 62,000 | 82,000 | 12,000 |
| | 2 | 72,000 | 50,000 | 46,000 | 64,000 | 58,000 | 72,000 | Separated |
| | 3 | 72,000 | 50,000 | 46,000 | 62,000 | 52,000 | 58,000 | |
| | 4 | 70,000 | 50,000 | 44,000 | 60,000 | 48,000 | Separated | |
| | 5 | 70,000 | 48,000 | 42,000 | 60,000 | 42,000 | | |
| | 6 | 68,000 | 48,000 | 44,000 | 58,000 | 38,000 | | |
| | 7 | 68,000 | 50,000 | 42,000 | 56,000 | 36,000 | | |
| | 8 | 66,000 | 48,000 | 42,000 | 58,000 | 36,000 | | |
| | 9 | 64,000 | 46,000 | 42,000 | 56,000 | 34,000 | | |
| | 10 | 64,000 | 46,000 | 40,000 | 54,000 | Separated | | |
| Rate of viscosity change (%) | | 13.5 | 11.5 | 16.7 | 18.2 | — | — | — |

As the results of the above temperature cycle tests, the oil type emulsion compositions of Examples 1 to 8 as the emulsifiers the polyorganosiloxane-polyoxyalkylene block copolymers according to the present invention having molecular structures within the specific range showed excellent stability to temperature changes including cooling to low temperatures of up to −10° C. On the other hand, the samples of Comparative Examples 1 and 4 employing the block copolymers having polyoxyalkylene chains as side chains only both showed great drop in the viscosity; while the samples of Comparative Examples 2 and 5 employing block copolymers having siloxane chains of high polymerization degrees and the samples of Comparative Examples 3 and 6 employing block copolymers of low polymerization degrees all underwent phase separation attributed to temperature changes.

According to the present invention, there are obtained water-in-oil type silicone emulsion compositions having excellent stability to temperature changes, particularly to temperature changes including low temperature regions of −5° C. or lower. Further, the silicone emulsion compositions of the present invention do not lose stability even if they are incorporated with components having a tendency to impair stability of the emulsions, such as salts.

The basic composition of the water-in-oil type silicone emulsion compositions of the present invention shows excellent texture when applied as cosmetics to the skin and is highly safe against the skin. Accordingly, the compositions of the present invention are useful as cosmetics, particularly for such applications as they are stored in containers respectively under refrigeration and are taken out of refrigerators together with the containers repeatedly when they are used.

Further, the water-in-oil type silicone emulsion compositions of the present invention can be incorporated with large amounts of polyhydric alcohols employed as humectants and the like, and they are stable as described above even if large amounts of salts employed as astringent agents which are antiperspirant components are added thereto. Therefore, they are useful as various kinds of skin-care products including milky lotions such as moisture lotions and emollient lotions; packs such as jelly packs and paste packs; creams such as vanishing creams, emollient creams and cold creams; and cleansing preparations such as cleansing creams and cleansing foams, as well as, various kinds of antiperspirative deodorants.

It should be apparent to those skilled in the art that the present invention may be embodied in many other specific forms without departing from the spirit or scope of the invention. Therefore, the present examples are to be considered as illustrative and not restrictive, and the invention is not to be limited to the details given herein, but may be modified within the scope of the appended claims.

What is claimed is:

1. A water-in-oil silicone emulsion composition comprising:

(A) at least one polyorganosiloxane;

(B) at least one polyorganosiloxane-polyoxyalkylene block copolymer represented by the formula (I):

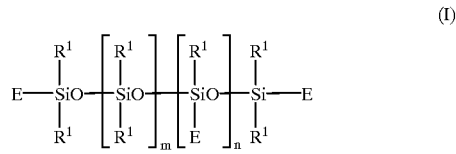

(I)

wherein each $R^1$ is methyl or phenyl; E is a group of the formula (II):

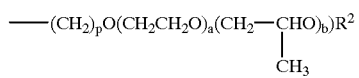
(II)

wherein $R^2$ represents a hydrogen atom, an acyl group or an alkyl group having 1 to 4 carbon atoms; p is an integer of 3 to 6; a is an integer of 2 to 50; b is an integer of 0 to 50; and a+b is a integer of 5 to 100, m is an integer of 300 to 600; n is an integer of 1 to 30; and m+n is an integer of 300 to 600; and (C) water wherein said emulsion is stable to a temperature cycle including cooling to −5° C. or lower.

2. The composition according to claim 1, further comprising a salt.

* * * * *